US006438425B1

(12) United States Patent
Miller et al.

(10) Patent No.: US 6,438,425 B1
(45) Date of Patent: Aug. 20, 2002

(54) TEXTURED SILICONE TUBING FOR ELECTRICAL PACING LEADS

(75) Inventors: Jennifer P. Miller, Elk River; Michael J. Ebert, Fridley; Joseph J. Klein, Plymouth; Richard D. Ries, Stillwater, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/416,971

(22) Filed: Oct. 12, 1999

(51) Int. Cl.[7] ................................................ A61N 1/05
(52) U.S. Cl. ..................... 607/122; 607/116; 600/373; 600/374
(58) Field of Search ................................ 607/122, 123, 607/126, 131, 116, 115; 600/373, 374, 375

(56) References Cited

U.S. PATENT DOCUMENTS

| 4,106,512 A | 8/1978 | Bisping |
| 4,269,198 A | 5/1981 | Stokes |
| 4,355,646 A | 10/1982 | Kallok et al. |
| 4,961,954 A | 10/1990 | Goldberg et al. |
| 5,358,517 A | 10/1994 | Pohndorf et al. |
| 5,531,781 A | * 7/1996 | Alferness et al. ............ 607/122 |
| 5,584,873 A | 12/1996 | Shoberg et al. |
| 5,779,699 A | * 7/1998 | Lipson ........................... 60/41 |
| 5,830,329 A | 11/1998 | Stewart et al. |
| 5,935,159 A | 8/1999 | Cross, Jr. et al. |
| 5,957,965 A | * 9/1999 | Moumane et al. ........... 607/117 |
| 5,968,087 A | * 10/1999 | Hess et al. .................... 607/127 |
| 6,119,037 A | * 9/2000 | Kellogg et al. ................ 604/21 |
| 6,249,708 B1 | * 6/2001 | Nelson et al. ............... 607/122 |

* cited by examiner

Primary Examiner—Kennedy Schaetzle
(74) Attorney, Agent, or Firm—Girma Wolde-Michael

(57) ABSTRACT

An implantable lead having a silicone rubber lead body which has a reduced coefficient of friction on an internal or external surface. The reduction in coefficient of friction is accomplished by extruding a tubular lead body to define a plurality of small parallel longitudinally extending grooves on the inner or outer surface of the lead body. The grooves may be formed by means of a die having inwardly or outwardly directed projections that form the grooves during the extrusion process. The formation of the grooves during extrusion provides a lead body having a lower coefficient of friction without the necessity of additional manufacturing process steps and without additional manufacturing costs.

14 Claims, 4 Drawing Sheets

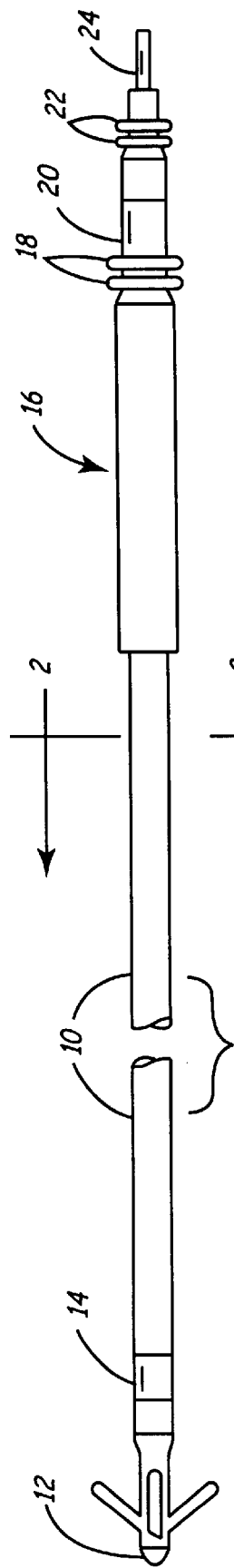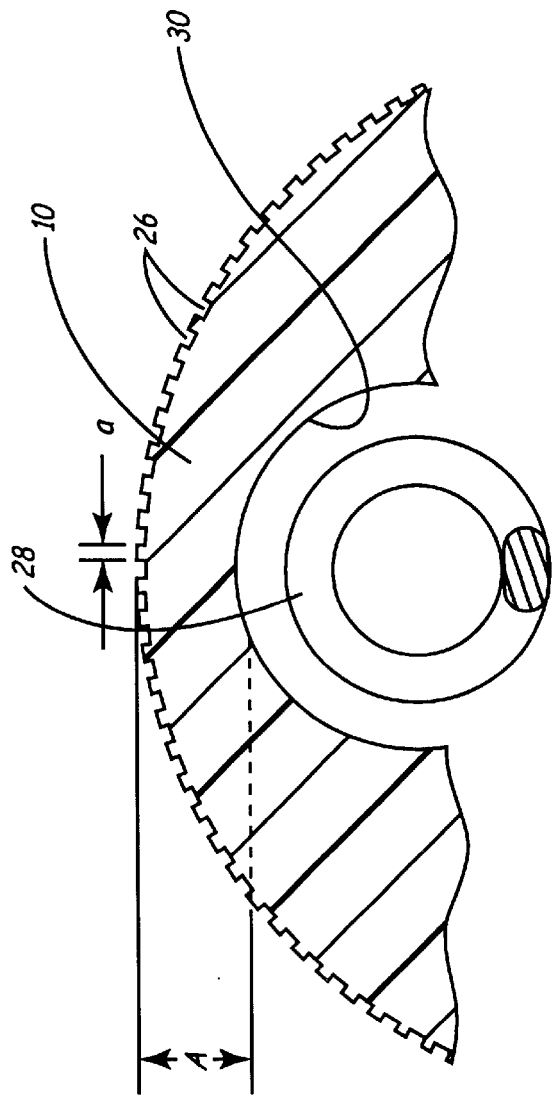
FIG. 1
FIG. 2

TEXTURED SILICONE TUBING FOR ELECTRICAL PACING LEADS

BACKGROUND OF THE INVENTION

The present invention relates generally to medical catheters and leads, and more particularly implantable electrode leads for use with implantable cardiac pacemakers or other implantable stimulators.

The vast majority of electrode leads for use in conjunction with cardiac pacemakers, nerve stimulators and cardioverter defibrillators have had tubular lead bodies fabricated either of silicone rubber or polyurethane. Leads with tubular silicone rubber lead bodies are illustrated in U.S. Pat. No. 5,935,159, issued to Cross et al. and U.S. Pat. No. 5,584,873, issued to Shoberg et al. Leads with tubular polyurethane lead bodies are illustrated in U.S. Pat. No. 4,269,198, issued to Stokes and U.S. Pat. No. 4,355,646, issued to Kallok et al. Silicone rubber has the advantage of being extremely durable and biostable within the human body. However, even when wetted with blood, it is difficult to pass two leads with silicone rubber lead bodies down the same blood vessel, due to the high coefficient of friction of silicone rubber. In leads employing rotating conductors for advancement of helical electrodes, commonly referred to as "screw-in" leads, the high coefficient of friction of silicone rubber makes efficient transfer of torque to the helical electrode more difficult.

There have been a number of techniques proposed to deal with this problem, including coating or lining a lead body with a material to reduce its coefficient of friction, for example as in U.S. Pat. No. 4,961,954 issued to Goldberg et al. or U.S. Pat. No. 5,358,517 issued to Pohndorf et al. An alternative is to treat the inner or outer surface of the silicone rubber lead body in some fashion to produce a lower coefficient of friction, for example, as disclosed in U.S. Pat. No. 5,830,329 issued to Stewart et al.

Both the above approaches have the disadvantage that they add complexity and cost to the process of manufacturing the silicone rubber lead body.

SUMMARY OF THE INVENTION

The present invention is directed to an implantable lead having a silicone rubber lead body that has a reduced coefficient of friction on an inner and/or outer surface thereof. The reduction in coefficient of friction is preferably accomplished by extruding a tubular lead body to define a plurality of small parallel longitudinally extending grooves on the inner or outer surface of the lead body. The grooves are preferably on the order of 0.5 microns to one millimeter in width and 1 micron to 20% of the wall thickness of the leady body in depth and are arranged around the internal or external circumference of the lead body relatively evenly spaced from one another. The grooves preferably have centers that are angularly displaced from one another by less than about 45 degrees, more preferably by less than about 20 degrees. The grooves are preferably sized so that they are spaced from one another no more than about 10%, preferably no more than about 5% of the external or internal circumference of the lead body. The grooves may be formed by means of a die having inwardly or outwardly directed projections that form the grooves during the extrusion process. Other methods of forming the grooves may also be employed. The formation of the grooves during extrusion provides a lead body having a lower coefficient of friction without the necessity of additional manufacturing process steps and without additional manufacturing costs.

BRIEF DESCRIPTION OF THE DRAWINGS

FIG. 1 is a plan view of a first embodiment of a cardiac pacing lead employing the present invention.

FIG. 2 is a cross-sectional view through a portion of the body of the lead illustrated in FIG. 1.

DETAILED DESCRIPTION OF THE PREFERRED EMBODIMENTS

Figure 3:
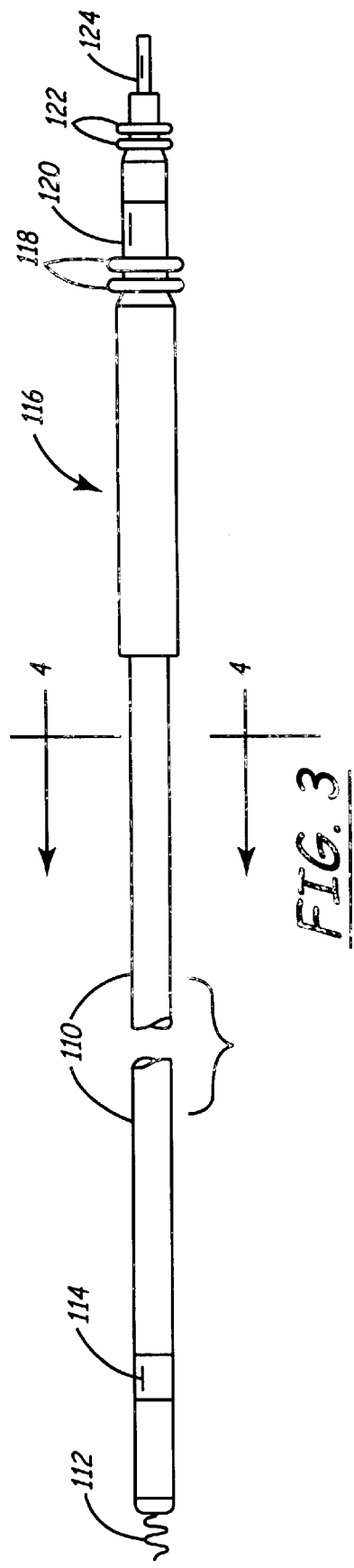
FIG. 3 is a plan view of a second embodiment of a lead embodying the present invention.

FIG. 1 is a cardiac pacing lead in overall form corresponds to presently available bipolar cardiac pacing leads. The lead is provided with an elongated silicone rubber lead body 10 that carries a pacing electrode 12 and an indifferent electrode 14 adjacent its distal end and which carries a connector assembly 16 at its proximal end. Connector assembly 16 carries a connector ring 20 coupled to ring electrode 14 by means of an elongated conductor located within lead body 10 and carries a connector pin 24 coupled to pacing electrode 12 by means of a second elongated conductor within lead body 10. Sealing rings 18 and 22 seal the connector assembly within the bore of an associated implantable pulse generator in a conventional fashion.

FIG. 2 is a cross-sectional view through the lead of FIG. 1. As illustrated, the lead of FIG. 1 is provided with longitudinal grooves 26 which run the length of the lead body 10 and are formed during the extrusion process. The grooves 26 are preferably sized so that they are spaced from one another by a distance "a" no more than about 10%, preferably no more than about 5% of the external circumference of the lead body 10. Grooves 26, for example, may have a width of approximately 0.5 microns to one millimeter and a depth of approximately one micron to 20% of the minimum wall thickness "A" of lead body 10. The grooves may in some embodiments be approximately the same magnitude as the sort of grooves that are often inadvertently produced as die extrusion due to imperfections in the die, commonly referred to as "die marks". In the case of the illustrated embodiment, however, the die surface which defines the external circumference of lead body 10 is deliberately provided with corresponding internally directed projections arrayed around the complete circumference of the die opening that correspondingly produce grooves distributed around the outer circumference of the lead body 10. The inwardly directed protrusions on the extrusion die may be formed by machining or by simply roughening the die surfaces, for example by means of an abrasive material. A coiled conductor 28 is visible within internal lumen 30 of the lead body 10. Leads manufactured with external longitudinal grooving as described above display a substantially reduced coefficient of friction in blood, allowing two leads to more easily be passed down the same vein into the heart.

FIG. 3 is a plan view of a second embodiment of a lead according to the present invention. The lead is provided with an elongated silicone rubber lead body 110 that carries a helical pacing electrode 112 and an indifferent electrode 114 adjacent its distal end. The lead carries a connector assembly 116 at its proximal end, which includes a connector ring 120 coupled to indifferent electrode 114 by means of an elongated conductor located within lead body 110 and a connector pin 124 coupled to fixation helix 112 by means of an elongated conductor located within lead body 110. In the fashion described in U.S. Pat. No. 4,106,512 issued to Bisping et al. and incorporated herein by reference in its entirety, the rotation of connector pin 124 causes corresponding rotation of the elongated conductor coupled thereto, in turn causing rotation and advancement of helical electrode 112 out of the distal end of the pacing lead.

Figure 4:
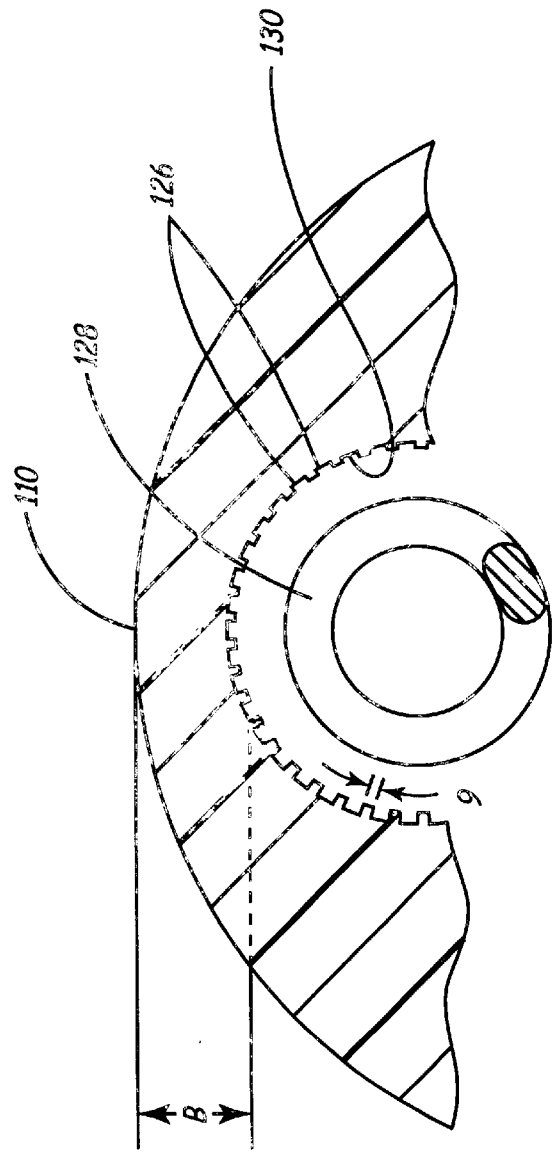
FIG. 4 is a cross-sectional view through a portion of the body of the lead of FIG. 3.

FIG. 4 is a cross-sectional view of a portion through the lead body 110. In this view it can be seen that grooves 126 are provided on the internal surface of lumen 130, formed within lead body 110. The grooves 126 are preferably sized so that they are spaced from one another by a distance "b" no more than about 10%, preferably no more than about 5% of the internal circumference of lumen 130. Grooves 126, for example, may have a width of approximately 0.5 microns to one millimeter and a depth of approximately one micron to 20% of the minimum wall thickness "B" of lead body 10. In the embodiment illustrated, grooves 126 provide for reduced frictional resistance to rotation of conductor 128 in conjunction with advancement of electrode 112 (FIG. 3). Grooves 126 are formed by means of outwardly directed protrusions on the die pin that defines lumen 130 during extrusion.

Figure 5:
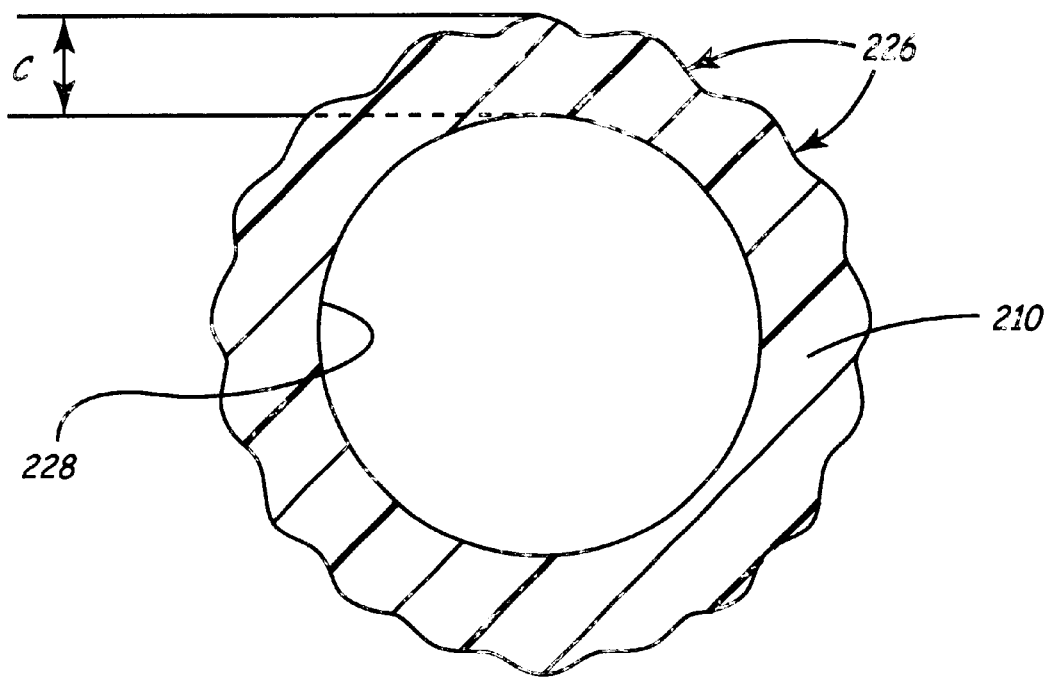
FIGS. 5–8 are cross-sectional views through portion of additional alternative embodiments of a lead body according to the present invention.

FIG. 5 illustrates tubular silicone rubber lead body 210, provided with 18 external grooves having an alternate configuration. The centers of the grooves 226 are displaced approximately 20 degrees from one another and are separated from adjacent grooves by less than about 5% of the circumference of the lead body 210 and have a depth less than about 20% of the thickness "C" of the wall of the lead body 210.

Figure 6:
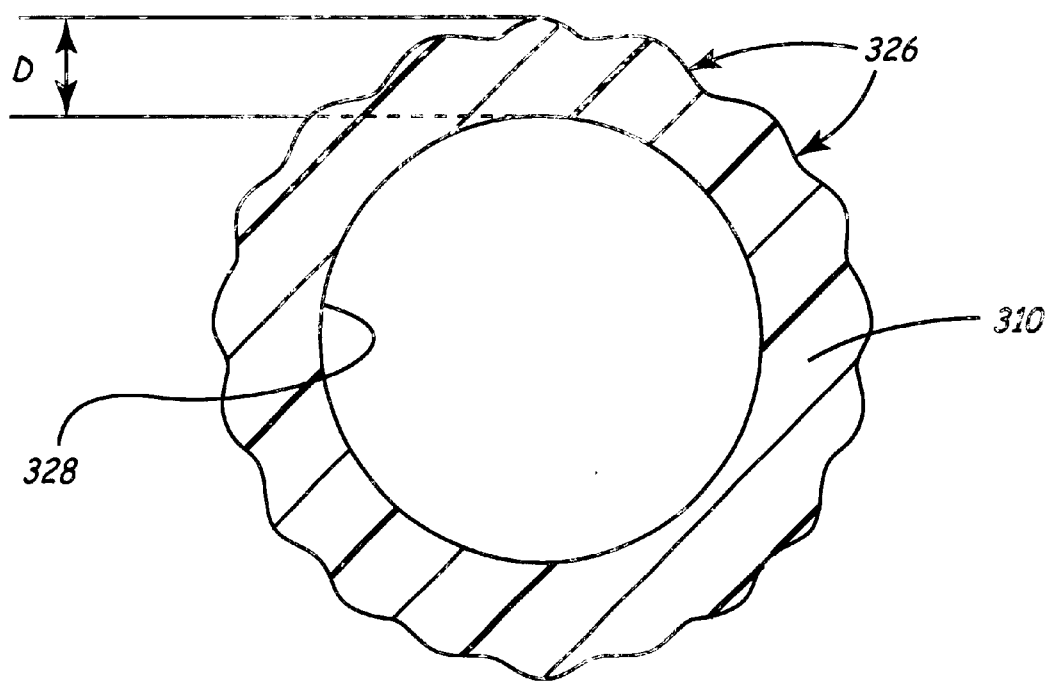

FIG. 6 illustrates tubular silicone rubber lead body 310 provided with 8 external grooves 326 having an alternate configuration. The centers of the grooves 326 are displaced approximately 45 degrees from one another and are separated from adjacent grooves by less than about 5% of the circumference of the lead body 310 and have a depth less than about 20% of the thickness "D" of the wall of the lead body 310.

Figure 7:
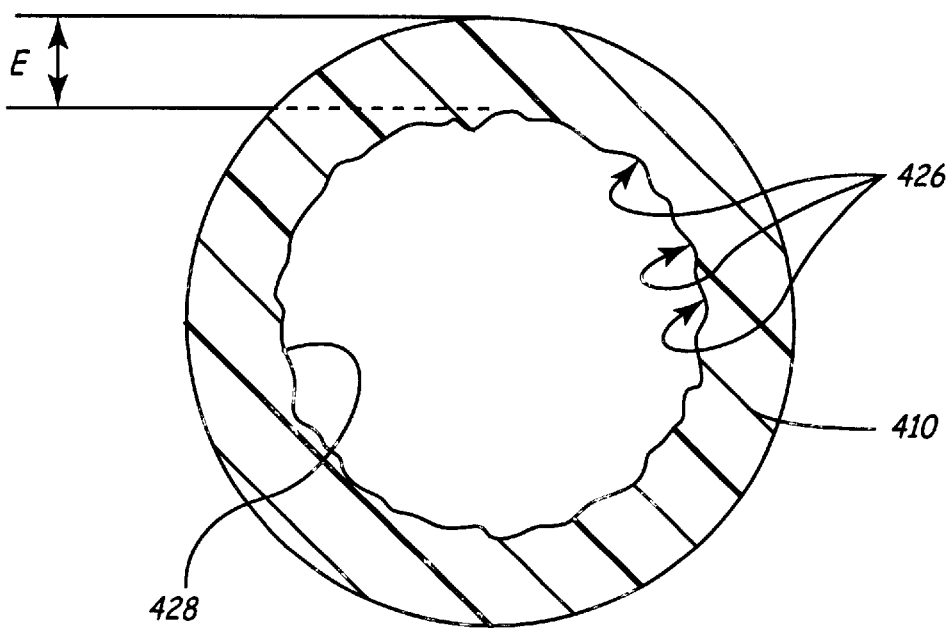

FIG. 7 illustrates tubular silicone rubber lead body 410 provided with an internal lumen 428 and internal grooves 426 having irregular configurations resulting from corresponding inwardly directed die protrusions formed by roughening the surface of the die pin which defines lumen 428. Although the grooves 426 as formed are irregularly spaced, the centers of the grooves 426 are generally displaced less than inapproximately 20 degrees from one another and are generally separated from adjacent grooves by less than about 10% of the internal circumference of the lumen 428 and have a depth less than about 20% of the thickness "D" of the wall of the lead body 410.

Figure 8:
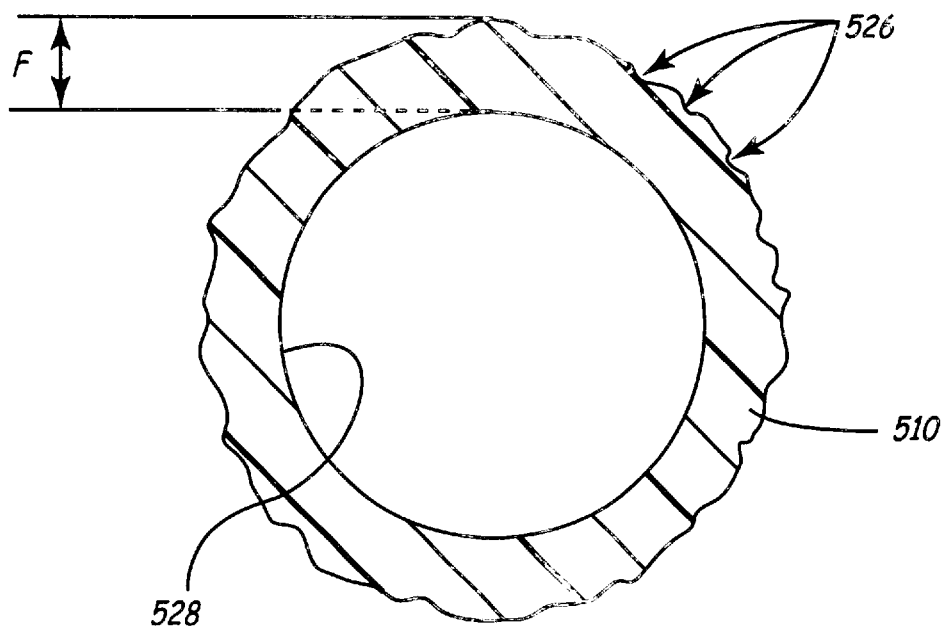

FIG. 8 illustrates tubular silicone rubber lead body 510 provided with an internal lumen 528 and external grooves 526, having irregular configurations resulting from corresponding inwardly directed die protrusions formed by roughening the die surface which defines the outer circumference of lead body 510. Although the grooves 526 as formed are irregularly spaced, the centers of the grooves are generally displaced approximately 20 degrees from one another and are generally separated from adjacent grooves by less than about 10% of the internal or external circumference respectively of the lead body and have a depth less than about 20% of the thickness "E" of the wall of the lead body 510.

In conjunction with the above specification, we claim:

1. An implantable lead of the type comprising an elongated silicone rubber lead body having an outer surface extending around an outer circumference of the lead body and a longitudinally extending inner lumen having an inner surface extending around an inner circumference and carrying an elongated electrical conductor within said lumen, wherein:

said inner surface is provided with longitudinally extending grooves arrayed around the circumference of said inner surface and displaced from one another by about 45 degrees or less.

2. The lead of claim 1 wherein:

said elongated electrical conductor is rotatably mounted within said lumen; and said lead further comprises an extendable, rotatable electrode at its distal end, coupled to said elongated conductor.

3. The lead of claim 1 or claim 2 wherein said grooves are displaced from one another by about 20 degrees or less.

4. The lead of claim 1 or claim 2 wherein said grooves are irregularly spaced from one another.

5. The lead of claim 1 or claim 2, wherein:

said lead body comprises a wall having a thickness and separating said lumen from the exterior surface of said lead body; and said grooves have a depth of about 20% of said thickness or less.

6. An implantable lead of the type comprising an elongated silicone rubber lead body having an outer surface extending around an outer circumference of the lead body and carrying therein an elongated electrical conductor, wherein:

said outer surface is provided with longitudinally extending grooves arrayed around the circumference of said outer surface and wherein said grooves are irregularly spaced from one another.

7. An implantable lead of the type comprising an elongated silicone rubber lead body having an outer surface extending around an outer circumference of the lead body and carrying therein an elongated electrical conductor, wherein:

said outer surface is provided with longitudinally extending grooves arrayed around the circumference of said outer surface and displaced from one another by about 45 degrees or less;

said lead body comprises a wall having a thickness and separating said lumen from the exterior surface of said lead body; and wherein said grooves have a depth less than about 20% of said thickness.

8. An implantable lead of the type comprising an elongated silicone rubber lead body having an outer surface extending around an outer circumference of the lead body and a longitudinally extending inner lumen having an inner surface extending around an inner circumference and carrying an elongated electrical conductor within said lumen, wherein:

said inner surface is provided with longitudinally extending grooves arrayed around the circumference of said inner surface and spaced from one another by about 45 degrees or less.

9. The lead of claim 8 wherein:

said elongated electrical conductor is rotatably mounted within said lumen; and said lead further comprises an extendable, rotatable electrode at its distal end, coupled to said elongated conductor.

10. The lead of claim 8 or claim 9 wherein said grooves are spaced from one another by about 5% of said inner circumference or less.

11. The lead of claim 8 or claim 9 wherein said grooves are irregularly spaced from one another.

12. The lead of claim 8 or claim 9, wherein:
   said lead body comprises a wall having a thickness and separating said lumen from the exterior surface of said lead body; and
   said grooves have a depth of about 20% of said thickness or less.

13. An implantable lead of the type comprising an elongated silicone rubber lead body having an outer surface extending around an outer circumference of the lead body and carrying therein an elongated electrical conductor, wherein:
   said outer surface is provided with longitudinally extending grooves arrayed around the circumference of said outer surface and wherein said grooves are irregularly spaced from one another.

14. An implantable lead of the type comprising an elongated silicone rubber lead body having an outer surface extending around an outer circumference of the lead body and carrying therein an elongated electrical conductor, wherein:
   said outer surface is provided with longitudinally extending grooves arrayed around the circumference of said outer surface and spaced from one another by about 10% of said outer circumference or less; and
   said lead body comprises a wall having a thickness and separating an inner lumen from the outer surface of said lead body and wherein said grooves have a depth less than about 20% of said thickness.

* * * * *